United States Patent
Berger et al.

(10) Patent No.: US 11,468,042 B2
(45) Date of Patent: Oct. 11, 2022

(54) DATA MANAGEMENT UNIT FOR SUPPORTING HEALTH CONTROL

(71) Applicant: SANOFI, Paris (FR)

(72) Inventors: Lars Berger, Frankfurt am Main (DE); Anton Petkov, Frankfurt am Main (DE); Arnaud Sestier, Zürich (CH); Axel Teucher, Frankfurt am Main (DE); Artur Keil, Frankfurt am Main (DE); Marcus-Meinolf Dittrich, Witten-Bommern (DE); Mario Esser, Frankfurt am Main (DE); Fabio Ciancitto, Frankfurt am Main (DE)

(73) Assignee: Sanofi, Paris (FR)

( * ) Notice: Subject to any disclaimer, the term of this patent is extended or adjusted under 35 U.S.C. 154(b) by 538 days.

(21) Appl. No.: 16/468,476

(22) PCT Filed: Dec. 12, 2017

(86) PCT No.: PCT/EP2017/082310
§ 371 (c)(1),
(2) Date: Jun. 11, 2019

(87) PCT Pub. No.: WO2018/108854
PCT Pub. Date: Jun. 21, 2018

(65) Prior Publication Data
US 2021/0256008 A1     Aug. 19, 2021

(30) Foreign Application Priority Data
Dec. 13, 2016  (EP) .................................. 16306674

(51) Int. Cl.
*G06F 16/00*     (2019.01)
*G06F 16/23*     (2019.01)
(Continued)

(52) U.S. Cl.
CPC ......... *G06F 16/2379* (2019.01); *G16H 10/60* (2018.01); *G16H 50/30* (2018.01); *G16H 50/70* (2018.01); *G16H 20/10* (2018.01)

(58) Field of Classification Search
CPC .... G06F 16/2379; G16H 10/60; G16H 50/30; G16H 50/70; G16H 20/10
See application file for complete search history.

(56) References Cited

U.S. PATENT DOCUMENTS

| 7,570,980 B2 | 8/2009 | Ginsberg |
| 2007/0179352 A1 | 8/2007 | Randlov et al. |

(Continued)

FOREIGN PATENT DOCUMENTS

| EP | 2085029 | 8/2009 |
| EP | 2851821 | 3/2015 |

(Continued)

OTHER PUBLICATIONS

International Preliminary Report on Patentability in International Appln. No. PCT/EP2017/082310, dated Jun. 18, 2019, 11 pages.

(Continued)

*Primary Examiner* — Dinku W Gebresenbet
*Assistant Examiner* — Suman Rajaputra
(74) *Attorney, Agent, or Firm* — Fish & Richardson P.C.

(57) ABSTRACT

Data management units for supporting health control of a human or animal body. The units can include a processor adapted to process the following steps: i) if a number of previous measurement data referring to a corresponding tag (Continued)

stored in a data storage is less than a predetermined minimum value: a) no tag is automatically assigned to a new measurement value, or b) a corresponding tag chosen from a group of tags is automatically assigned to the new measurement value based on a first tagging calculation rule; and ii) if the number of the previous measurement data referring to a corresponding tag stored in the data storage is equal to or bigger than the predetermined minimum value, the corresponding tag chosen from a group of tags is automatically assigned to the new measurement value based on at least one second tagging calculation rule.

11 Claims, 8 Drawing Sheets

(51) Int. Cl.
    *G16H 10/60*     (2018.01)
    *G16H 50/30*     (2018.01)
    *G16H 50/70*     (2018.01)
    *G16H 20/10*     (2018.01)

(56) References Cited

U.S. PATENT DOCUMENTS

| | | |
|---|---|---|
| 2008/0255707 A1 | 10/2008 | Hebblewhite et al. |
| 2009/0240127 A1 | 9/2009 | Ray |
| 2015/0012223 A1 | 1/2015 | Aykroyd et al. |

FOREIGN PATENT DOCUMENTS

| | | | |
|---|---|---|---|
| JP | 2007-535974 | 12/2007 | |
| JP | 2009-532768 | 9/2009 | |
| WO | WO 2005/093629 | 10/2005 | |
| WO | WO 2007/112034 | 10/2007 | |
| WO | WO-2015040164 A1 * | 3/2015 | ............. G16H 40/63 |

OTHER PUBLICATIONS

International Search Report and Written Opinion in International Appln. No. PCT/EP2017/082310, dated Feb. 12, 2018, 13 pages.

* cited by examiner

DATA MANAGEMENT UNIT FOR SUPPORTING HEALTH CONTROL

CROSS REFERENCE TO RELATED APPLICATIONS

The present application is the national stage entry of International Patent Application No. PCT/EP2017/082310, filed on Dec. 12, 2017, and claims priority to Application No. EP 16306674.9, filed on Dec. 13, 2016, the disclosures of which are incorporated herein by reference.

TECHNICAL FIELD

The present disclosure relates to data management units, medical devices, methods for operating such units, respective computer programs, and computer program products, for supporting health control.

BACKGROUND

Diabetes mellitus is a group of metabolic diseases in which a person has high blood sugar, either because the pancreas does not produce enough insulin, or because cells do not respond to the insulin that is produced. The treatment of diabetes usually concentrates on keeping blood sugar levels as close to normal ("euglycemia") as possible, without causing hypoglycemia. This can sometimes be accomplished with diet, exercise, and use of appropriate medications (insulin in the case of type 1 diabetes; oral medications, as well as possibly insulin, in type 2 diabetes).

Some elements of the management of diabetes with insulin can include periodic checks of the glucose concentration in the blood performed by the patients themselves, in order to obtain regular information on the progress and success of the prescribed treatment. This understanding and patient participation can be vital, since the complications of diabetes may be far less common and less severe in patients who have well-managed blood sugar levels. With regard to this it can be considered that the blood glucose level fluctuates throughout the day and is directly influenced by the amount of insulin administered, as well as lifestyle factors such as the amount and kind of food that is consumed, the exercise level, and stress.

Therefore, the monitoring of the sugar level in the blood with a data management unit can serve a dual purpose: on the one hand it can provide the patient with information about the current status of glycemic control. On the other hand, the measured values can serve as information for the patient or a healthcare professional (HCP) to determine whether an adjustment in the medication, namely the amount of insulin to be taken, is indicated.

In order to achieve these goals or to get as close as possible to the desired glycemic control, it may be common practice that blood glucose (BG) measurement values are measured using a blood glucose meter (BGM) once or several times during the day, following a testing regime normally prescribed by an HCP. Typically, a data management unit, or a BGM including such data management unit, is used to record the individual BG values. From the measured BG values, ingested carbohydrates and previous administered doses of the medicament the user may determine the appropriate medication.

A special role can be played by the so-called fasting blood glucose measurement value (FBG). A fasting blood glucose measurement value is derived after several hours without eating (6 to 8 hours). The fasting blood glucose measurement value is typically taken in the morning before breakfast and is typically the most commonly performed test among insulin treated patients, as it can be used to assess the quality of the titration of long-acting basal insulin or analogs such as insulin glargine.

In order to adjust or to adapt the therapy, it can be helpful to record the results of all blood glucose measurements and to analyze these results with the data management unit. Additionally, the administered doses and/or the ingested carbohydrates may be recorded. Therefore, typically a portable monitor is used which may be able to measure the blood glucose level as well or which receives the measurement values from a blood glucose measurement device. A wireless or wired data transfer can be used to transport the results from the measurement device to the data management unit.

In addition to the mere monitoring of the blood glucose level diabetic individuals often have to maintain tight control over their lifestyle so that they are not adversely effected by, for example, irregular food consumption or exercise. Further, the HCP may need detailed information on the lifestyle of the patient to provide effective treatment or modification of treatment for controlling the disease. In former times, one of the ways of monitoring the lifestyle of a patient with diabetes has been for the individual to keep a paper logbook of their lifestyle. Currently, a number of portable electronic devices exist that can measure glucose levels in an individual and store the levels for recalling and uploading to another computer for analysis. Further, they provide functionality for storing lifestyle data for example by using a tag (or flag) associated to the individual measurement value.

Document EP 2 085 029 A1 refers to a method of operating an analyte measurement device having a display, user interface, processor, memory and user interface buttons. After measuring an analyte with the analyte measurement device the measurement value is displayed and the user is prompted to select a flag to associate the flag with the value. By pressing only one of the user interface buttons once, the flag is stored with the measurement value in the device.

Document U.S. Pat. No. 7,570,980 B2 discloses blood glucose measurement data stored in an array including associated time code information for each measurement and various other flags. These flags may correspond to specific time frames, date information, calibration check information etc. From the measured and flagged values the so called effective meal average value is calculated encompassing the measurement values that occur at specific times, for example one hour before and one hour after a specified meal time.

SUMMARY

The following description refers to diabetes as a health problem and the blood glucose level as the physiological parameter to be controlled in order to assess the effectiveness of the prescribed treatment. However, the systems and methods describe herein may also be used with regard to other health problems and for management of other physiological parameter data, for example (a) blood pressure in hypertensive heart disease, (b) cholesterol or lipoprotein profile in patients with risk factors for heart disease and stroke, (c) peak flow in asthmatic patients, or (d) coagulation in patients treated for hemophilia.

As flags or tags are effective means to facilitate an accurate assessment of the glucose control in a patient, they can be used in the analysis of patient self-monitored BG values. However, providing each measurement value with an associated tag information is sometimes too difficult and/or time consuming for the patient. Further, it is important to make sure that only the correct tag information is stored with the associated measurement value. If incorrect tag information is associated with a BG value, then the additional information can lead to a false assessment of the BG control when it is reviewed later by the HCP or patient.

For the insulin therapy, inter alia long-acting basal insulin, insulin or basal insulin analogues (e.g. insulin glargine) are used. It is possible to automate the calculation of the required dose of long-acting insulin by using algorithms which consider fasting blood glucose measurements and previous applied doses to propose a suitable dose to the patient. This is one example for the use of tags, as the fasting blood glucose measurements are chosen from the entirety of blood glucose measurements by the corresponding tag of each blood glucose measurement value. From above explanation, it is also evident that wrong associated fasting tags could lead to a wrong dose suggestion and may seriously harm the patient.

Therefore it can be desired to make tagging of BG measurement values easier for the user, while reducing the probability of wrong tagging.

The systems, devices, units, products, and methods described herein can be used to alleviate the aforementioned problems.

In at least one aspect of the present disclosure, a data management unit for supporting health control of a human body is provided. The unit includes:
a processor,
a receiving unit adapted to receive measurement data of a body property and connected to the processor, wherein a corresponding time stamp of each new measurement value is either received with the measurement value or determined by the receiving unit,
a data storage connected to the processor and adapted to store a first tagging calculation rule, at least a second tagging calculation rule and previous received measurement data (together with their corresponding time stamps), some of them with a corresponding tag referring to an event,
wherein after receipt of a new measurement value from the receiving unit the processor is adapted to process the following steps:
   if a number of the previous measurement data referring to a corresponding tag (of one specific event) stored in the data storage is less than a predetermined minimum value,
     no tag is automatically assigned to the new measurement value or
     the corresponding tag chosen from a group of tags is automatically assigned to the new measurement value based on the first tagging calculation rule,
   if the number of the previous measurement data referring to the corresponding tag (of one specific event) stored in the data storage is equal to or bigger than the predetermined minimum value the corresponding tag chosen from a group of tags is automatically assigned to the new measurement value based on the at least one second tagging calculation rule which is different from the first tagging calculation rule.

The data storage may be directly or indirectly connected to the processor, wherein an indirect connection may be realized, for example, via the receiving unit. Further, the corresponding tag with regard to the new measurement value of a body property is, for example, determined by comparing the time stamp of the new measurement value with the time stamps of the previous measurement data stored within the data storage as explained below.

Therein, measurement data is, for example, a recent measurement value of a body parameter, e.g. a blood glucose measurement value. Tagging makes data evaluation easier and the information contained within the data more specific.

With the tag referring to a pre-defined event (event tag), additional information associated with the measurement value is provided. The event tag may be added via data input, for example manually by the user, or automatically by the processor.

In some implementations, the choice of event tags for blood glucose measurement values includes the pre-meal or fasting tag, and at least one other tag referring to one of the following events: pre-meal breakfast or fasting, post-meal breakfast, pre-meal lunch, post-meal lunch, pre-meal dinner, post-meal dinner and bedtime. There is also the possibility that a no-tag (nil) is associated to the measurement value.

The time stamp associated to each new measurement value, which can be provided by a clock unit of the receiving unit, can include date and time information of a certain time point during the measurement process resulting in the respective measurement value, for example, the completion of the measurement process or receipt of the new measurement value by the data management unit. In some implementations, the time stamp is associated by the measurement unit and is transferred to the processor with the respective measurement value. In case the new measurement value is not associated with a respective time stamp by the measurement unit, the time stamp can assigned by the clock unit after receipt of the measurement value.

The pre-determined minimum value is, in some implementations, at least 3 for one tag (referring to a specific event). In some implementations, the pre-determined minimum value is at least, 10 for one tag (referring to a specific event), or at least 15 for one tag (referring to a specific event). This can ensure that this tag is only automatically assigned by the at least one second tagging calculation rule if a sufficient statistical population of previous measurement data referring to this tag is available. The pre-determined minimum value may be set by the user and/or a HCP, for example as a selection from a pre-determined range going, for example, from 3 to 200. The predetermined minimum value may be the same for all tags or different for two different tags.

For example, the following time ranges for tagging pre-selection (i.e. time ranges of a day, each between a specific starting time and a specific end time) used in a first tagging calculation rule may be defined:
pre-meal breakfast or fasting: 5:00 a.m. to 8:59 a.m.
post-meal breakfast: 9:00 a.m. to 10:59 a.m.
pre-meal lunch: 11:00 a.m. to 1:59 p.m.
post-meal lunch: 2:00 p.m. to 3:59 p.m.
pre-meal dinner: 4:00 p.m. to 6:59 p.m.
post-meal dinner: 7:00 p.m. to 8:59 p.m.
bedtime: 9:00 p.m. to 11:59 p.m.
night time or no tag: 12:00 a.m. to 4:59 a.m.

Additionally, or alternatively, time ranges (i.e. time ranges of a day each between a specific starting time and a specific end time) for tags that are not meal-related events may be provided and treated by the processor analogously. In some implementations, the choice of event tags includes an exercise tag. For example, if the exercise tag has been assigned to BG values measured around 3:00 p.m. or measured between 3:00 and 5:00 p.m. on several Tuesdays, the exercise tag can be automatically assigned to the next new measurement value at measured 3:05 p.m. on a Tuesday based on the first or second tagging calculation rule. Ranges for tagging pre-selection may be defined for not meal-related events such as exercise as well. In some implementations, a minimum duration must be kept for any time range for tagging pre-selection. In some implementations, the minimum duration is one hour.

At least part of the time ranges for tagging pre-selection may be set and changed by the user and/or HCP using for example the settings menu of the data management unit.

The time range for tagging pre-selection (i.e. a pre-defined time range between a specific starting time and a specific end time) for the at least one predefined event refers to a time range which is used to support the user during tagging as follows. After receipt of a new measurement value and assignment of an associated time stamp, if necessary, the processor compares, in the first tagging calculation rule, the time information of the associated time stamp with the time range for tagging pre-selection. If the time information lies within the time range, the corresponding tag of the predefined event is automatically selected and provided at the display for user confirmation. In other words, a predefined time range (time range for tagging pre-selection) is assigned with one predefined event. The time stamp of a new measurement value is compared with the predefined time range and the tag for the assigned event is automatically selected in case the time stamp is within the predefined time range. For example, if the current time range for the pre-breakfast and fasting blood glucose tag includes the range between 5:00 a.m. and 8:59 a.m. as indicated above, then for each measurement value measured within this time range the fasting or pre-breakfast tag is automatically selected (for example, if no other measurement value of that day includes the fasting tag) and may be confirmed by the user afterwards as described below in detail. It is further possible for the user to change the automatically selected tag or to select the no-tag.

Hence, as in many cases, a tag is automatically selected and may only need to be confirmed by the user, and thus the data management unit reduces the number of steps for tag selection. Accordingly, it is easier for the user to assign a tag with the measurement value. Further, as with the above explained data management unit the most probable tag for the measurement value is automatically selected, the data management unit reduces the possibility for incorrect tagging.

In some implementations of the first tagging calculation rule, the time range for tagging pre-selection of a certain event may be different for working days and non-working days (i.e. the starting time and/or the end time of the time range for tagging preselection of one certain event differ for working days and for non-working days). In this case, the determination whether the associated time stamp of the new measurement value is within the time range for tagging pre-selection can be based, not only on the time information of the time stamp, but also on the date and/or on the weekday information.

As mentioned above, the data management unit may include a clock unit, wherein the clock unit determines the corresponding time stamp for the new measurement value. This can ensure determination of a reliable and accurate time stamp. The clock unit can be provided with the receiving unit or as separate unit connected with the receiving unit.

In some implementations, the data management unit further includes a display connected to the processor and adapted to visibly and/or audibly and/or tangibly display received messages or information, wherein the display is further adapted to display the automatically assigned tag and requests the user to confirm the tag or to change and confirm the tag, and after the receiving unit receives user confirmation, the processor initiates storing the new measurement value and the corresponding confirmed tag in the data storage. Thus, the user can control whether an automatically assigned tag is an appropriate tag. Incorrect tagging, especially in exceptional situations, can be avoided. Audibly and/or tangibly displaying information facilitates use of the data management unit by visually impaired users.

In some implementations of the data management unit, the first tagging calculation rule and/or the at least one second calculation rule includes a comparison of the time stamp of the new measurement value with at least a pre-defined first time range for tagging pre-selection for a first event and at least a pre-defined second time range for tagging pre-selection for a second event. This exhibits a quick automatic association of tags without complex calculations.

In some impelementations, the at least one second tagging calculation rule includes adaption of the first time range for tagging pre-selection (i.e. its starting time and/or its end time) and the at least one second time range for tagging pre-selection (i.e. its starting time and/or its end time) according to the tags and the time stamps of the stored previous measurement data. In this embodiment, the information gathered about correlations between tags and time stamps of the previous measurement data is used efficiently to improve automatic assignment of tags.

In some implementations, the at least one second tagging calculation rule considers the stored previous measurement data and/or the new measurement value of a body property. This increases the reliability and accuracy of automatic tagging. In particular, even if a correct tag for the new measurement value cannot be identified solely on the basis of its time stamp and the pre-defined time ranges for tagging pre-selection, nonetheless the suitable tag can be automatically chosen by considering the measurement data gathered, e.g. the BG values.

The at least one second tagging calculation rule can consider a first usual time point of a first event and at least a second usual time point of a second event. This can improve the predictive power regarding to the correct tag to be assigned to the new measurement value. In some implementations, the usual time point for the first event and the usual time point for the second event are median time points of a plurality of time stamps of measurement values tagged with the first or second event, respectively. Using a median of a plurality of time stamps can be more robust against outliers that may otherwise cause rapid variations of the calculated "usual time point". Alternatively, the usual time point may be calculated from the plurality of time stamps of measurement values tagged with the respective event by determining the arithmetic, geometric or harmonic mean value of the time stamps.

In some implementations, the at least one second tagging calculation rule considers the absolute time difference of the time stamp of the new measurement value from the closest past time point of all usual time points (ARTP), namely the first usual time point and all second usual time points, and the absolute time difference of the time stamp of the new measurement value from the closest future time point of all usual time points (ARTF), namely the first usual time point and all second usual time points. The closest past time point is one time point of all usual time points which is prior to the time stamp of the new measurement value (if only 24 hours of a day are taken into account) and has the least time difference to the time stamp of the new measurement value.

ARTP is the absolute time difference between the new measurement value and the closest past time point. The closest future time point is one time point of all usual time points which is after the time stamp of the new measurement value (if only 24 hours of a day are taken into account) and has the least time difference to the time stamp of the new measurement value. ARTF is the absolute time difference between the new measurement value and the closest future time point. These differences are simple and effective criteria for automatic tagging which may not require complex calculations.

In some implementations, the at least one second tagging calculation rule considers the absolute time difference between ARTP and ARTF and compares this time difference with a predetermined percentage rate of the bigger one of ARTP and ARTF and further
    if the absolute time difference between ARTP and ARTF is larger than the predetermined percentage rate of the bigger one of ARTP and ARTF, the at least one second tagging calculation rule assigns the tag of the event of the closer one of the closest future time point and the closest past time point to the new measurement value
    if the absolute time difference between ARTP and ARTF is smaller than or equal to the predetermined percentage rate of the bigger one of ARTP and ARTF, the second tagging calculation rule uses another criteria in order to assign a tag to the new measurement value.

In this manner, it can be assured that a tag is only assigned by the second tagging calculation rule solely on the basis of time stamp comparison if the difference between ARTP and ARTF is sufficiently significant. If this is the case, other information may not be needed and superfluous calculations can be avoided. However, if this is not the case, the another criteria employed and described below in one example considers additional and/or different information to assign the tag. Consequently, automatic assignment of wrong tags to a new measurement value due to statistical deficiencies can be reliably avoided.

The another criteria can consider the new measurement value. This can ensure that a tag is automatically assigned even if the time stamp of the new measurement value is not significant enough for automatic assignment. As the measurement values for the measured body property, for example the blood glucose value, may usually be different for the various lifestyle situations or events to which the tags are related, this information is considered for assigning a tag to the new measurement value.

In some implementations, the second calculation rule calculates in the another criteria
    the absolute difference between the new measurement value and the median of the previous measurement data referring to the event of the closest past time point (ARBGP) and
    the absolute difference between the new measurement value and the median of the previous measurement data referring to the event of the closest future time point. (ARBGF),
wherein
    if ARBGP is bigger than ARBGF then the second calculation rule assigns the tag of the event of the closest future time point,
    if ARBGP is smaller than ARBGF then the calculation rule assigns the tag of the event of the closest past time point,
    if ARBGP is equal to ARBGF then the calculation rule compares ARTP and ARTF, wherein
        if ARTP is bigger than ARTF the calculation rule assigns the tag of the event of the closest future time point,
        if ARTP is smaller than or equal to ARTF the calculation rule assigns the tag of the event of the closest past time point.

The term "medicament", as used herein, refers to a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound includes at least one peptide for the treatment and/or prophylaxis of diabetes mellitus or complications associated with diabetes mellitus such as diabetic retinopathy, wherein in a further embodiment the pharmaceutically active compound includes at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-α30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N—(ω-carboxyheptadecanoyl)-des(B30) human insulin and B29-N—(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39), des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative; or
an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Trp(O2)25, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(02)25, Asp28] Exendin-4(1-39)-(Lys)6-NH2; or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

In a further embodiment the processor is further adapted to receive a data input from the user related to the physiological parameter, wherein the data input includes for example at least one of the following parameters:
- occurrence or number of hypoglycemic events after a predetermined point in time, e.g. a last use of the medical device or the time stamp of the last (previous) measurement value,
- occurrence or number of hyperglycemic events after a predetermined point in time, e.g. the last use of the medical device or the time stamp of the last (previous) measurement value,
- size of the injected medicament dose after a predetermined point in time, e.g. the last use of the medical device or the time stamp of the last (previous) measurement value, wherein the injected medicament dose is automatically selected as the dose of the last (previous) suggested dose.

The above mentioned data input may be facilitated, for example after tagging. These additional parameters may be used for further calculations, data display, or for the assessment of the disease.

In another embodiment, in particular in the case in which the data management is realized as an app within a smartphone, an internet connection, a GSM connection, a GPS receiver or other means for determining the actual location and/or the time-zone of the device may be provided. Hence, the device includes for example a GSM receiver, a GPS receiver or module, a radio broadcast receiver capable of interpreting an RDS signal and/or a radio clock receiver like DCF 77 in order to determine the local time. Further, in case that the method is realized as an app within a smartphone a built-in GPS module may determine its location using public hotspots.

The data management unit may therefore keep track of the time, e.g. by implementing an electronic timer, or a first clock and calendar function. To enable tagging of a glucose measurement as a fasting glucose measurement, the device may have to determine, whether the last blood glucose measurement that was related to a meal, such as the "after dinner" glucose measurement, dates back at least, for example, eight hours. In order to determine this time difference correctly without influence of time change because of travelling, the device may have to account for time shifts that may occur for example when travelling to a different time zone. For this purpose, the device may include a separate second clock which is separate from the clock showing the actual time to the user. In order to determine a time difference reliably, the second clock may not be adjustable by the user. The second clock may derive its energy from a separate battery (for example a coin cell) which is separate from the battery or other energy source of the device and in particular separate from the energy source of the first clock.

Analogously, the above problem can also be alleviated by a medical device including the above explained data management unit with the same advantages.

For the same reason as explained above the problem is alleviated by a method for operating a data management unit for supporting health control, the unit including:
a processor, and
a data storage connected to the processor and adapted to store a first tagging calculation rule, at least a second tagging calculation rule and previous received measurement data, some of them with a corresponding tag referring to an event, wherein the method includes the steps
    receiving a new measurement value of a body property by a receiving unit, which is connected to the receiving unit,
    either receiving a corresponding time stamp of the new measurement value with the measurement value or determining it by the receiving unit,
    then, the processor proceeds with the following steps
        if a number of the previous measurement data referring to a corresponding tag stored in the data storage is less than a predetermined minimum value,
            no tag is automatically assigned to the new measurement value or
            the corresponding tag chosen from a group of tags is automatically assigned to the new measurement value based on the first tagging calculation rule, if the number of the previous measurement data referring to a corresponding tag stored in the data storage is equal to or bigger than the predetermined minimum value the corresponding tag chosen from a group of tags is automatically assigned to the new measurement value based on the at least one second tagging calculation rule which is different from the first tagging calculation rule.

And the above problem is solved by a computer program for operating a data management unit, the unit including:
a processor, and
a data storage connected to the processor and adapted to store a first tagging calculation rule, at least a second tagging calculation rule and previous received measurement data, some of them with a corresponding tag referring to an event, wherein the computer program includes the steps
receiving a new measurement value of a body property by a receiving unit, which is connected to the receiving unit,
either receiving a corresponding time stamp of the new measurement value with the measurement value or determining it by the receiving unit,
then, the program proceeds with the following steps
if a number of the previous measurement data referring to a corresponding tag stored in the data storage is less than a predetermined minimum value,
no tag is automatically assigned to the new measurement value or
the corresponding tag chosen from a group of tags is automatically assigned to the new measurement value based on the first tagging calculation rule,
if the number of the previous measurement data referring to a corresponding tag stored in the data storage is equal to or bigger than the predetermined minimum value the corresponding tag chosen from a group of tags is automatically assigned to the new measurement value based on the at least one second tagging calculation rule rule which is different from the first tagging calculation rule.

The above method and computer program may be realized with the embodiments as mentioned above with regard to the data management unit.

The above problem is further solved by computer program product including a computer-readable medium bearing computer program code embodied therein for use with a computer, wherein the computer program code includes the above mentioned computer program.

The above-mentioned advantages as well as other advantages of various aspects of the present disclosure will become apparent to those of ordinary skill in the art by reading the following detailed description with the explanation of the accompanying drawings. All features described above and below and/or illustrated per se or in any combination form the subject-matter of the disclosure, independent of their inclusion in the claims or their back-reference.

BRIEF DESCRIPTION OF THE FIGURES

Exemplary embodiments of the present disclosure are described herein with reference to schematic drawings, in which.

DETAILED DESCRIPTION

The following paragraphs will describe various embodiments of the disclosure. For exemplary purpose, the embodiments are outlined in relation to a medical device with regard to blood glucose level measurement. However, the used terminology and the description of the embodiments with respect to the medical device or the method are not intended to limit the principles and ideas of the disclosure to such a single device or method and may be adapted to other physiological values accordingly.

Figure 1:
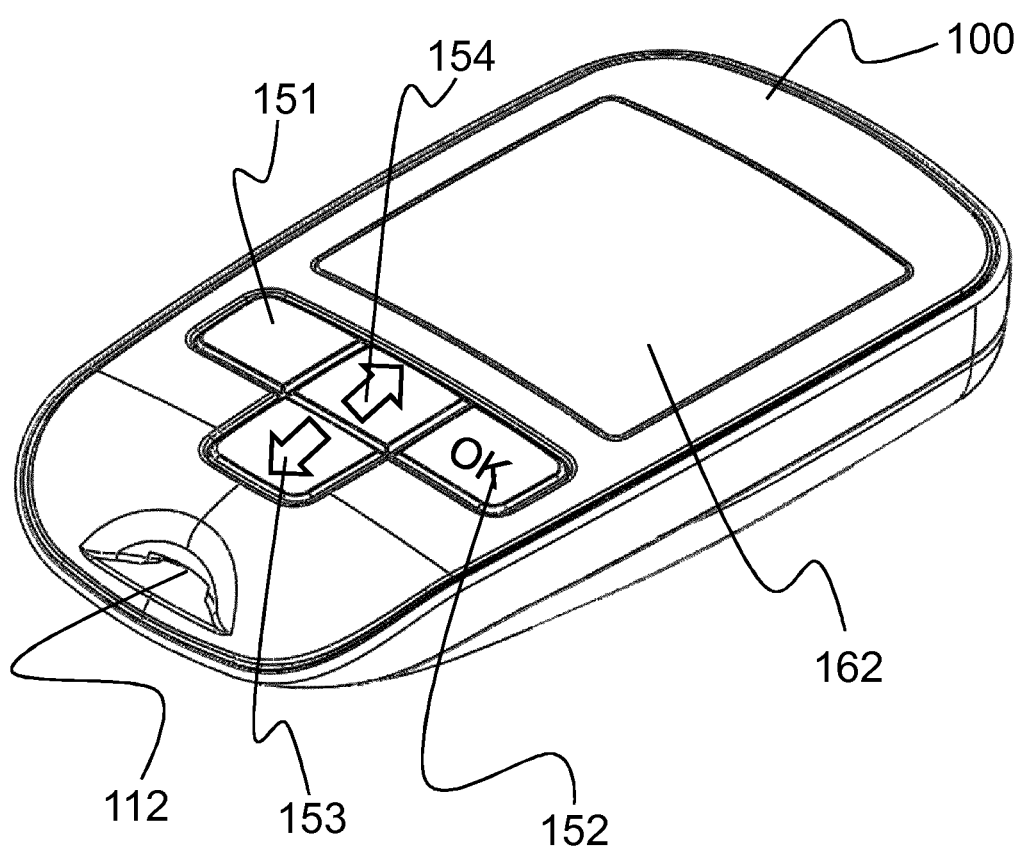
FIG. 1 shows a medical device according to one or more embodiments of the disclosure in a perspective view.
Figure 2:
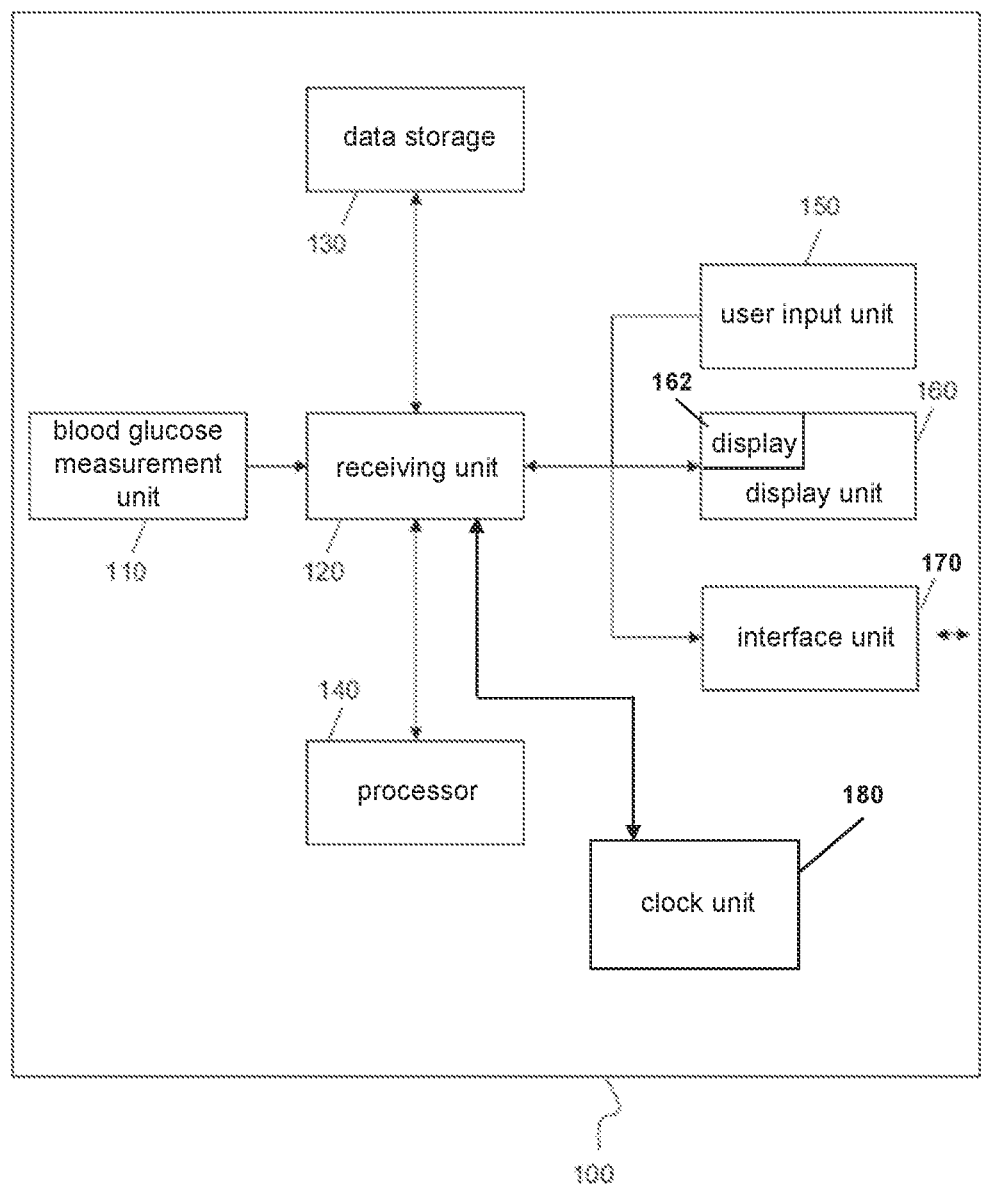
FIG. 2 shows a diagram of the medical device as shown in FIG. 1.

FIG. 1 is a schematic drawing and FIG. 2 is a schematic diagram of the medical device 100 according to one or more embodiments of the disclosure. The medical device 100 includes a blood glucose measurement unit 110, which is arranged to measure the blood glucose level. Further, the measurement unit 110 includes an interface and a slot 112 for inserting a test strip.

The blood glucose measurement unit 110 is connected to a receiving unit 120, which is arranged to forward e.g. blood glucose measurement data received from blood glucose measurement unit 110 to a data storage 130 (storage unit or means or memory), such as a Flash memory. Alternatively, the receiving unit 120 may retrieve stored data such as e.g. blood glucose value data from the data storage 130 and forward it to a processor 140 (processing unit or means), such as a microcontroller or microprocessor or any other functional unit capable of processing data, a digital signal processor, and/or the like. Alternatively, the receiving unit 120 directly forwards the blood glucose value data received from the blood glucose measurement unit 110 to the processor 140.

Receiving unit 120 is further connected to a user input unit 150 of a user interface. The user input unit 150 is arranged to receive input from the user of the medical device 100 for example by key 151, confirmation key (OK button) 152, key 153 for scrolling down (downward button) and key 154 for scrolling up (upward button). The user input data are forwarded from the user input unit 150 to the receiving unit 120, which either forwards it to the processor 140 or to the data storage 130.

Furthermore, the user interface of medical device 100 includes a display unit 160 with a display 162, which is connected to the receiving unit 120 as well. In some implementations, the display unit 160 receives data to be displayed by the display 162 from the receiving unit 120 or the processor 140.

In some implementations, the medical device 100 additionally includes a further interface 170, for example a wired interface such as a serial port, a Universal Serial Bus (USB)

interface, a mini-USB interface, or a wireless interface such as an infrared (e.g. an IRDA) interface, a Bluetooth™ interface, and/or the like, in order to receive data and/or to transmit data. The interface 170 is, in some implementations, connected to the receiving unit 120 in order to receive data from the receiving unit 120 and/or to forward data to the receiving unit 120.

Additionally, the receiving unit 120 of the medical device 100 includes a clock unit 180 which provides a date and time information, based on a clock generator in some implementations, which may be displayed at the display 162. Further, the clock unit 180 provides date and time information in particular for generating a time stamp for an associated blood glucose measurement.

The receiving unit 120, the data storage 130, the processor 140, the input unit 150, the display unit 160, the clock unit 180, and optionally the interface 170 form the data management unit according to the disclosure.

As outlined above, the medical device 100, in some implementations, includes the blood glucose measurement unit 110. In some implementations, the blood glucose measurement unit 110 is arranged to measure the blood glucose level in the blood of e.g. the user by testing a drop of blood on a test strip that is inserted into the slot 112. The measurement may be conducted using e.g. a well-known electrochemical method. Full insertion of the test strip in the slot 112 may be detected by a respective sensor. The measured blood glucose value is transformed to blood glucose value data and forwarded, in some implementations, immediately or on demand to the receiving unit 120. Alternatively, the blood glucose measurement unit 110 is arranged to measure the blood glucose level of the user via infrared diagnosis or an alternative contactless measurement method.

According to a further alternative (not depicted in FIG. 1) the blood glucose measurement unit 110 is implanted in the body of the user of the medical device and forwards the data to the receiving unit 120 either via a wired connection or via a wireless connection. In an embodiment, such an implanted blood glucose measurement unit 110 is a continuous measurement sensor e.g. based on a chip which may allow a continuous closed loop control. In the latter case the medical device includes two parts, one part contains the measurement unit 110 and the other part the remaining units of the medical device, i.e. the data management unit. The blood glucose measurement unit 110, in some implementations, forwards the blood glucose measurement value data to the receiving unit 120 via interface 170. According to a further alternative the medical device does not include a blood glucose measurement unit which measures the blood glucose values but only the data management unit, and receives blood glucose value data from an external unit.

The measurement of the blood glucose measurement is, in some implementations, triggered by the receiving unit 120 which sends a respective signal to the blood glucose measurement unit 110. According to one alternative, the receiving unit 120 receives a trigger signal generated by user input which is received via user input unit 150 or based on a signal from the slot 112 detecting a test strip. Alternatively, the trigger signal is generated automatically by the clock unit 180 or by the processor 140. Further alternatively, only the transmission of measurement values is triggered by the user input or the processor 140 via the user input 150.

In some implementations, the receiving unit 120 is represented e.g. by the input ports and output ports of a microprocessor or a bus system managing the data handling between several functional units. This includes bus systems, such as e.g. Advanced Microprocessor Bus Architecture bus systems implemented in a microprocessor or external bus systems connected to a microprocessor. Via the receiving unit 120, data are retrieved from the blood glucose measurement unit 110, the data storage 130 immediately or on demand and forwarded to the processor 140, to the display unit 160 or to the interface 170. Moreover, the receiving unit 120 forwards control signals, such as trigger signals or control signals e.g. to the blood glucose measurement unit 110, the display unit 160 or the interface 170.

The data storage 130 is arranged to store data entered via the user input unit 150, a plurality of blood glucose measurement data received from the blood glucose measurement unit 110 together with the time stamp and/or at least one event tag associated to each measurement data, data calculated from the plurality of blood glucose measurement values processed by the processor 140 and/or data received via interface 170.

Further the data storage 130 stores parameter data like an associated time range for tagging pre-selection regarding for example a fasting tag which assigns a respective blood glucose measurement value to the fasting event.

In one embodiment, such a time range for tagging pre-selection is defined using a center time and a duration, wherein the time range includes the time around the center time with the size of the duration in both directions. For example, the predefined fasting window for assigning the fasting tag is defined with a duration of 3 hours and a predefined usual fasting time at 7 a.m., so that the time range for fasting tagging pre-selection encompasses the time between 4:00 a.m. and 9:59 a.m.

Additionally, for example the data storage 130 stores the following preset time ranges for the indicated events for tagging pre-selection:
pre-meal breakfast or fasting: 5:00 a.m. to 8:59 a.m.
post-meal breakfast: 9:00 a.m.to 10:59 a.m.
pre-meal lunch: 11:00 a.m. to 1:59 p.m.
post-meal lunch: 2:00 p.m. to 3:59 p.m.
pre-meal dinner: 4:00 p.m. to 6:59 p.m.
post-meal dinner: 7:00 p.m. to 8:59 p.m.
bedtime: 9:00 p.m. to 11:59 p.m.
night time or no tag: 12:00 a.m. to 4:59 a.m.

The data storage 130 also stores predefined data, which at least partly may be changed by the user, such as above mentioned time ranges for tagging pre-selection for a number of pre-set events.

Further mealtime time ranges, usual fasting times and fasting windows may be set by the user "Settings" mode of the medical device 100 at any time. In some implementations, time ranges may also be deleted by the user "Settings" mode.

Furthermore, data storage 130 is arranged to provide the stored data to the processor 140, to the display unit 160 and/or to the interface 170. The data storage 130 is, in some implementations, implemented as a semiconductor memory such as a Flash memory. Alternatively, it is implemented as a hard disk memory or an on-chip memory of the processor 140.

The user input unit 150 is, in some implementations, implemented as a keyboard including one or more push buttons 151, 152, 153, 154. The keyboard may include one or more soft keys, wherein the function of the soft keys may be displayed on the display 162. Alternatively, the user input unit 150 is a key board or a touch screen. Additionally or alternatively, the user input unit 150 includes a microphone for receiving speech input so that data can be entered via speech input.

After facilitating a blood glucose measurement a tag may be automatically associated to the measurement value referring to lifestyle data as explained below in detail. The automatically selected tag may be changed by pressing the up or down keys 153, 154 scrolling upwards or downwards through the different tags which are for example the fasting tag, pre-meal breakfast tag, post-meal breakfast tag, pre-meal lunch tag, post-meal lunch tag, pre-meal dinner tag, post-meal dinner tag, bedtime tag, nighttime tag and no-tag, respectively, referring to a measurement value which is a fasting blood glucose value, a pre-meal breakfast blood glucose value, a post-meal breakfast blood glucose value, etc. and a blood glucose value that cannot be associated to one of the previous lifestyle parameters.

The display unit 160, in some implementations, includes an LCD, LED or OLED display 162. In some implementations, the display displays a number of alphanumerical characters so that e.g. the presently measured blood glucose value can be displayed together with additional instructions for the user. Alternatively or additionally, the display unit 160 includes a graphic display in order to display graphs or graphics such as icons. Further the display of the display unit 160 may include a touchscreen.

The interface 170 is, in some implementations, a wireless interface, such as IRDA, Bluetooth™ GSM, UMTS, Zig-Bee, or WI-FI, etc. Alternatively, the interface is a wired interface, such as a USB port, mini-USB port, serial data port, parallel data port, etc., for receiving and transmitting data. In a further alternative embodiment the medical device 100 does not include an interface 170.

According to another alternative embodiment, medical device 100 includes a memory card reader or a memory card reader interface. The memory card reader is, in some implementations, adapted to read information from a memory card, such as a Flash memory card, or any type of SIM card. For this purpose, the memory card includes a memory, wherein at least one of a selected algorithms together with corresponding parameters, a history of the blood glucose values and/or insulin doses administered, etc. is stored. Thus, in the case that the medical device 100 has a defect, the relevant data may still be stored on the memory card which can be easily removed from the memory card reader of the medical device 100 and transferred to a new medical device 100. Moreover, the memory card 100 may be used in order to provide information on the history of the treatment to e.g. an HCP.

In the case that the memory card is a SIM card providing subscriber identification for a mobile communication network and the interface unit 170 is additionally a mobile communication interface, additional functions of the medical device 100 can be unlocked by the provider of the SIM card via a telecommunication channel. This offers the possibility that the medical device 100 can communicate with other telecommunication devices via predefined channels, such as UMTS or GSM. Via the international mobile subscriber identity, also called IMSI, stored in the SIM card, the medical device 100 identifies itself within the network and, thus, can be addressed via the network. In such a case the medical device 100 can be easily checked, remote controlled, updated, monitored, etc., via interface unit 170, e.g. by addressing the mobile communication unit with a phone number.

Furthermore, the medical device 100 is able to transmit data via SMS, e-mail or via mobile internet connection. Moreover, this offers the possibility to locate the medical device 100 in an emergency case.

In the case that the blood glucose measurement unit 110 is a sensor which is e.g. implanted a dose delivery unit with an insulin pump forming an automatic delivery system may be additionally provided.

Figure 5:
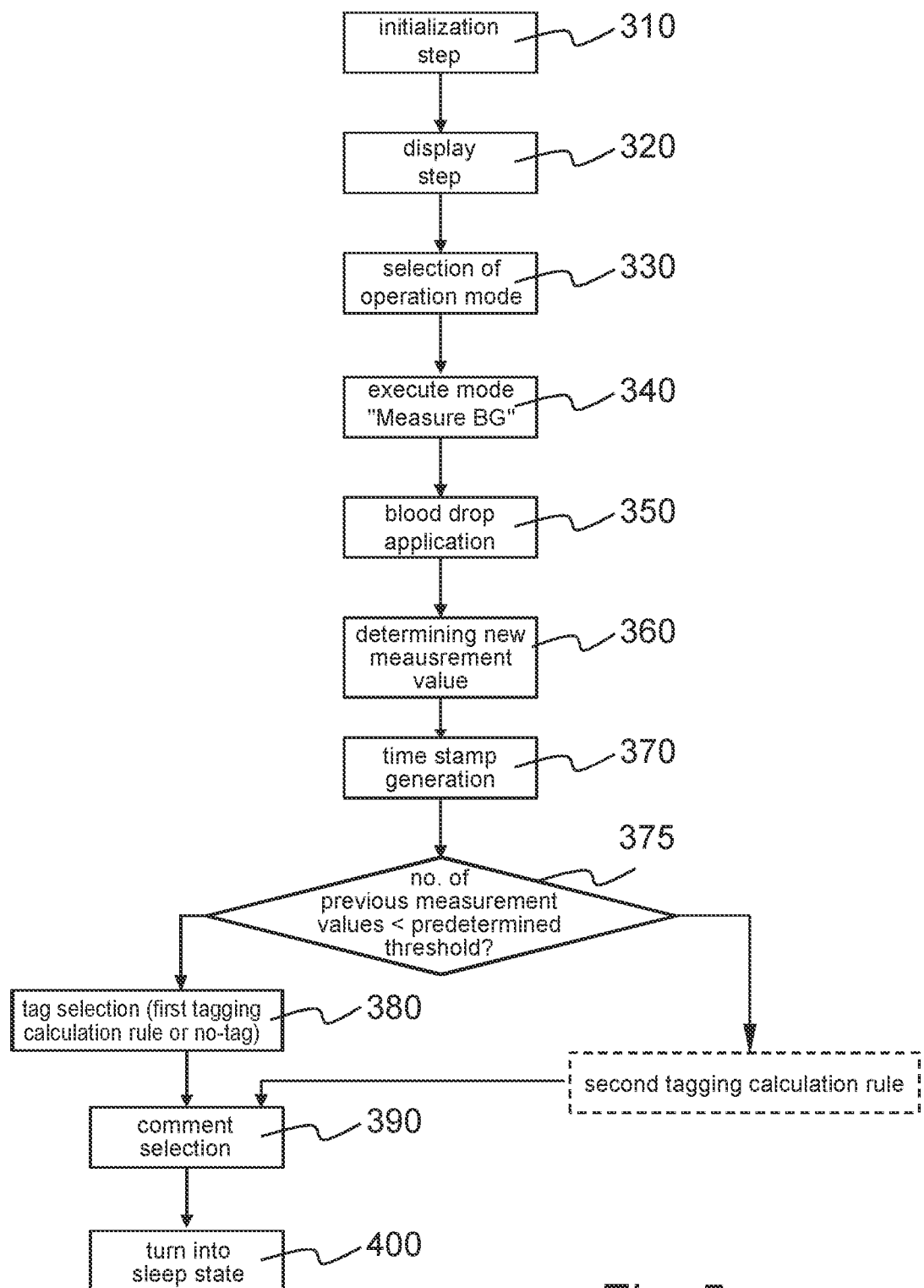
FIGS. 5 and 6 depict a flow diagram of a method realized by the medical device in the "Measure BC" mode.

As shown in FIG. 5, the medical device 100 or the data management unit is capable to perform a number of process steps. According to one embodiment after switching on, e.g. by pressing a key 151, 152, 153 or 154, the confirmation key 152 for a predetermined time, or detection of a test strip within the slot 112, the medical device 100 performs initialization step 310 for initializing the functional components of the medical device 100. After this, the different operation modes which are implemented in the medical device 100, are displayed in the display step 320, e.g. "Measure BC", "Logbook", and/or "Settings".

In step 330 the user selects one of the displayed operation modes via the user input unit 150, for example by means of the keys 153, 154 for scrolling down or up, and confirms the selection using the confirmation key 152.

In step 340 the selected operation mode is executed. As an example the mode "Measure BC" is selected for executing a blood glucose measurement. Upon execution of this mode the user/patient is requested to provide a test strip with a blood sample.

In the "Logbook" mode the history of previous measurements and statistical results may be calculated and displayed.

The "Settings" mode allows the user to define and change some parameters of the medical device 100 stored in the data storage 130, e.g. time ranges for tagging pre-selection for a number of pre-set events.

After selecting the mode "Measure BC" this operation mode is executed, beginning in step 350 with the application of a drop of blood to the test portion of the test strip which is inserted in slot 112 of the medical device 100.

According to an alternative version of the operation process steps 310 to 340 may be skipped in the case that a specific operation mode, e.g. the "Measure BC" mode, is preselected. In this case, after initialization, the preselected operation mode, which is either preselected by the user or automatically selected in accordance with a specific event, for example the detection of a fully inserted test strip in slot 112, the operating process executes the preselected one or more operation modes, for example the mode "Measure BC", and proceeds with the following step 350 and asks the user to apply a drop of blood.

Now in step 360 the measurement unit 110 determines e. g. by a known electrochemical or an optical method the blood glucose level a new measurement value and displays this new measurement value at the display 162. Therefore, the new measurement value is received by the input unit 120 and transmitted to the display unit 160 and the processor 140.

At the same time, in the next step 370 the clock unit 180 generates a time stamp for the new measurement value including a date and time information of the absolute time of the measurement (e.g. its finishing). The time stamp is also displayed in display 162 and both, the new blood glucose measurement value and the associated time stamp is transferred by receiving unit 120 to the data storage 130 in order to store these data.

Now, in step 375 the processor determines the number of previous measurement values which refer to a corresponding tag stored in the data storage 130. Therein, if there is a no-tag stored with one previous measurement value, this measurement values are not counted. Additionally, the determination of the number of previous measurement data with tag may be restricted to a predefined time period, for example the last 90 days, in order to exclude older measurement values.

If the number of previous measurement data is determined, the processor 140 compares this number with a predetermined minimum value (for example 15) stored in the data storage 130. If the number of previous measurement data referring to a corresponding tag is less than the predetermined minimum value (for example 15 for a specific tag), then the processor automatically assigns the corresponding tag chosen from a group of tags to the new measurement value based on a simple first tagging calculation rule which is explained below in detail. If the number of previous measurement data referring to a corresponding tag stored in the data storage 130 is equal to or bigger than the predetermined minimum value, the processor 140 automatically assigns the corresponding tag chosen from a group of tags to the new measurement data based on a more complex second tagging calculation rule which is explained in detail below.

If the automatic assignment of the corresponding tag is based on the first tagging calculation rule the processor 140 proceeds with the next step 380.

In this step the processor 140 compares the absolute time of the time stamp of the present blood glucose measurement value with the time ranges for tagging pre-selection of the events stored in the data storage 130. If the time stamp of the new measurement value, in particular the time information of the time stamp, lies within the current time range of e.g. for post-meal lunch event or within the fasting window around the usual fasting time automatically the fasting tag or the post-meal lunch tag, respectively, is provided for confirmation by the user and displayed with a respective sign 168, for example a struck out, empty apple or a bitten apple, respectively, at display 162 (see FIG. 3).

In order to show that a confirmation is necessary, the tag sign 168 displayed on display 162 is blinking/flashing. Now, the user may confirm the fasting tag for example by pressing the confirmation key 152. Alternatively, the user may change the tag using the up and down keys 153, 154, for example into the pre-meal breakfast tag, the post-meal breakfast tag etc. or the no-tag (nil). If the correct tag is chosen the user confirms the tag by pressing the confirmation key 152. By confirmation of the tag with the confirmation key 152 the flashing of the displayed tag sign is stopped and the tag sign is displayed continuously without blinking. In this state, pressing the up/down keys 153, 154 will not change the tag. Then, the processor 140 initiates storage of the associated, confirmed tag with regard to the recent measurement value in the data storage 130 via receiving unit 120.

If in step 380 the processor 140 cannot find any range for tagging pre-selection or the fasting window which refers to the time information of the time stamp of the present measurement value, the no-tag is automatically selected.

After pressing the confirmation key 152, if the user presses the confirmation key again, the tag will start flashing again and pressing the up/down key will again allow the user to change the tag again as explained above.

Figure 6:
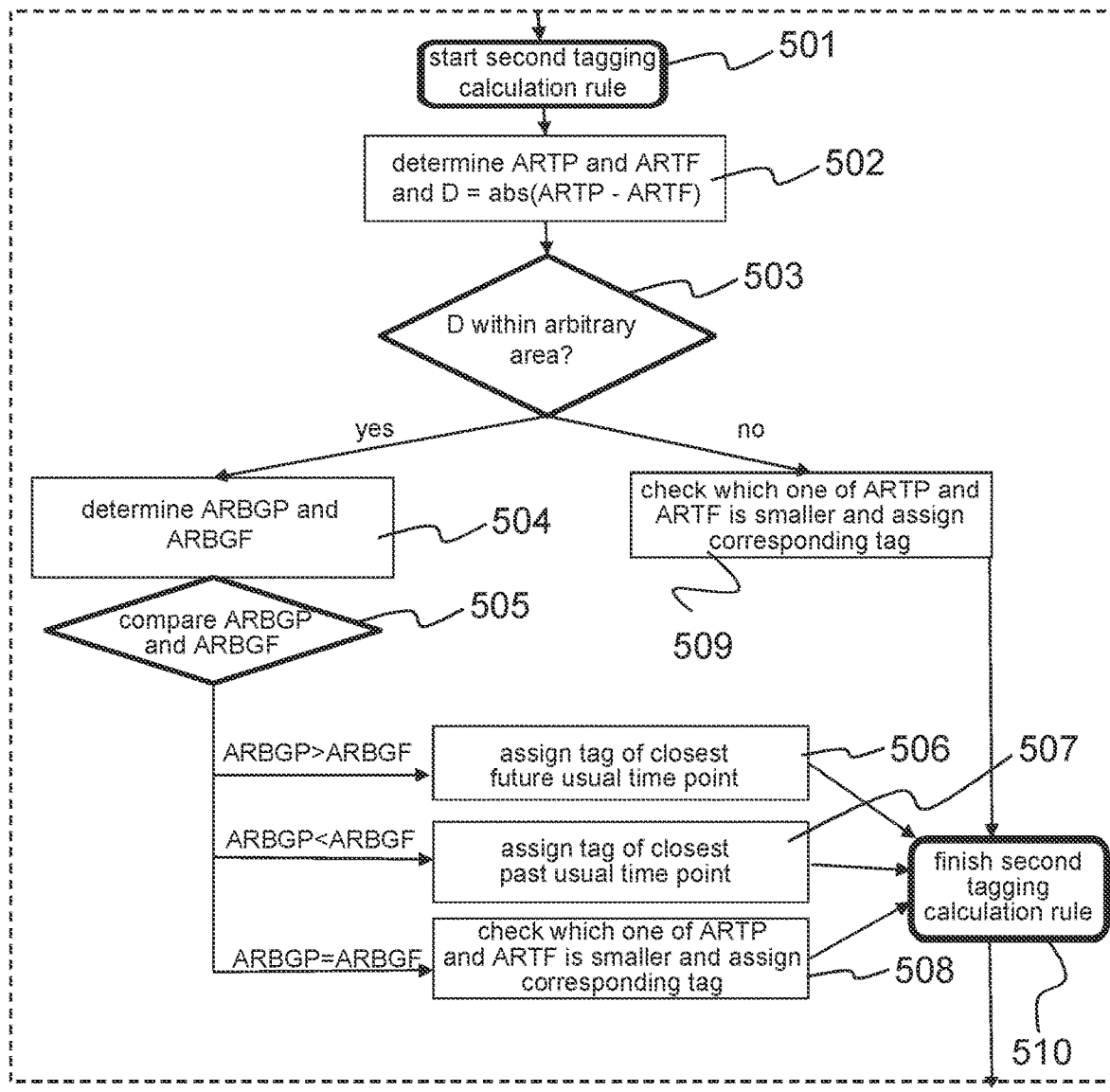

If the number of previous measurement data referring to a corresponding tag is equal to or bigger than the predetermined minimum value the processor 140 proceeds after step 375 with step 501 and starts the second tagging calculation rule branch of the diagram depicted in FIG. 6. This tagging calculation rule can be more complex and may need a certain number of tagged measurement values.

Figure 7:
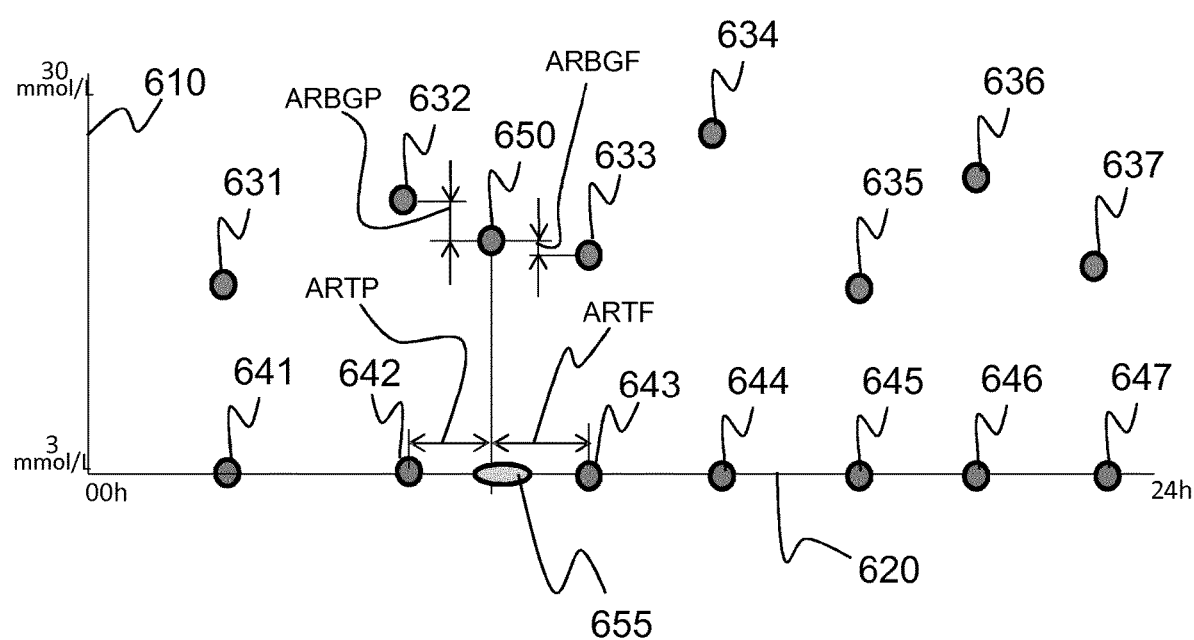
FIG. 7 depicts a diagram in which the usual time points of the events and the new measurement value are shown within a period of one day with the respective median measurement data within the blood glucose measurement range (in mmol/L)

Therein, in the next step 502 according to the absolute time of the time stamp of the new measurement value the processor 140 determines the closest past time point of the usual time points and the closest future time point of the usual time points which are depicted over a 24h time period in the diagram of FIG. 7 showing the absolute time of the time stamp at the x-axis 620 and the blood glucose value at the y-axis 610.

FIG. 7 depicts on the x-axis 620 the usual fasting time 641, the usual post-breakfast time 642, the usual pre-lunch time 643, the usual post-lunch time 644, the usual pre-dinner time 645, the usual post-dinner time 646 and the usual bed time 647. For example the usual fasting time 641 is determined by the processor 140 as the median time value of the time values of all previous blood glucose measurement values tagged with the fasting tag stored in the data storage 130 or of the previous blood glucose measurement values tagged with the fasting tag within a predetermined previous period of time (e.g. last 90 days).

For example, the data storage 130 may contain three blood glucose measurement values that are associated with a fasting tag, lie within the predetermined time range and are associated with the following exemplary time stamps:
1) 7:45 a.m.
2) 7:30 a.m.
3) 8:30 a.m.

In this case, the median time value of the time values of these fasting blood glucose measurements and therefore the usual fasting time 641, is 1) 7:45 a.m.

Analogously, the usual post-breakfast time 642 is a median time value of the time values of all previous blood glucose measurement values tagged with the post-breakfast tag stored in the data storage 130 of all stored measurement values or of the previous blood glucose measurement values tagged with the post-breakfast tag within a predetermined previous period of time (e.g. last 90 days). The remaining usual event times 643 to 647 are analogously calculated with regard to the respective event.

The corresponding median measurement value for the measurements including the fasting tag is designated with the reference number 631.

For example, the three fasting blood glucose measurement values from before are:
1) 125 mg/dL
2) 95 mg/dL
3) 100 mg/dL Then, the median measurement value 631 for the fasting tag is 3) 100 mg/dL.

Accordingly, the reference number 632 refers to the median measurement value for the post-breakfast tag, the reference number 633 to the median measurement value for the pre-lunch tag, the reference number 634 to the median measurement value for the post-lunch tag, the reference number 635 to the median measurement value for the pre-dinner tag, the reference number 636 to the median measurement value for the post-dinner tag and the reference number 637 to the median measurement value for the bedtime tag.

The diagram in FIG. 7 also shows with reference number 650 the new measurement value, which is entered into the diagram according to the absolute time of its time stamp and according to its blood glucose value with reference to the x-axis 620 and the y-axis 610. From the diagram in FIG. 7 it can be derived that the closest past time point of the usual time points 641, 642, 643, 644, 645, 646, 647 is the usual post-breakfast time 642. The future time point of the usual time points 641, 642, 643, 644, 645, 646, 647 which is closest to the absolute time of its time stamp is the usual pre-lunch time 643.

Figure 8:
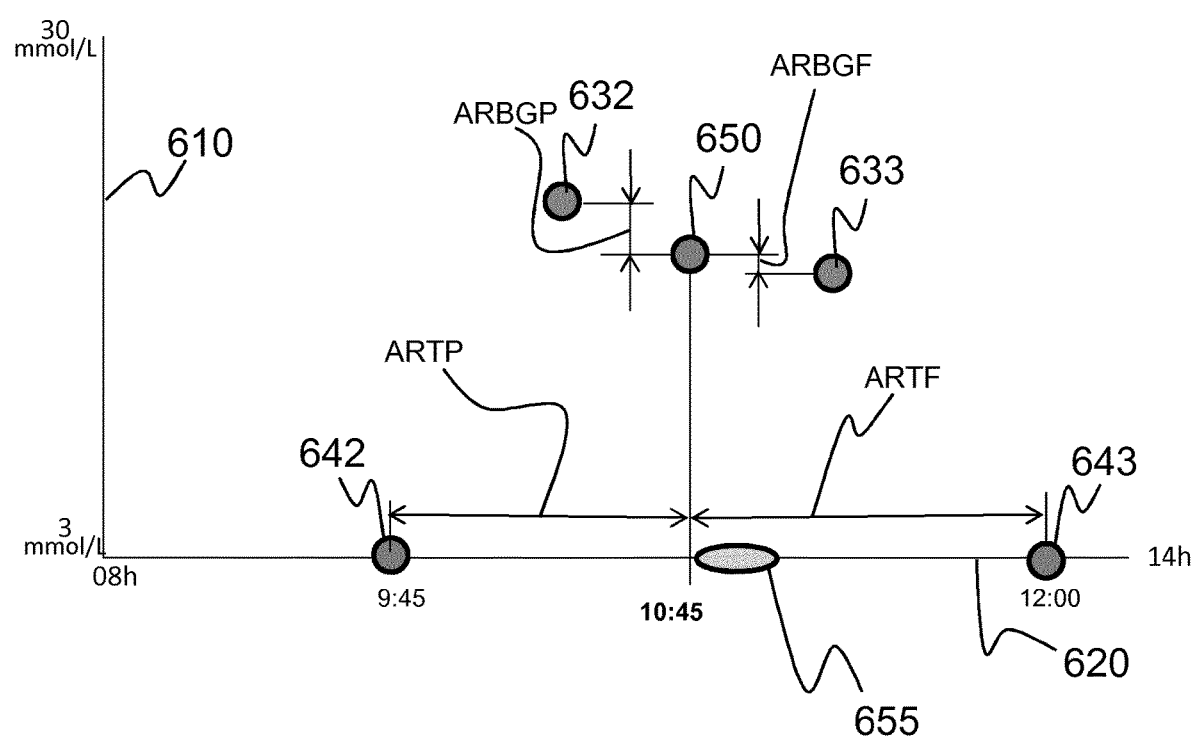
FIGS. 8 and 9 show the comparison of a new measurement value with the closest usual time points in a diagram in which the usual time points of the events are shown within a section of one day with the respective median measurement data within the blood glucose measurement range (in mmol/L).
Figure 9:
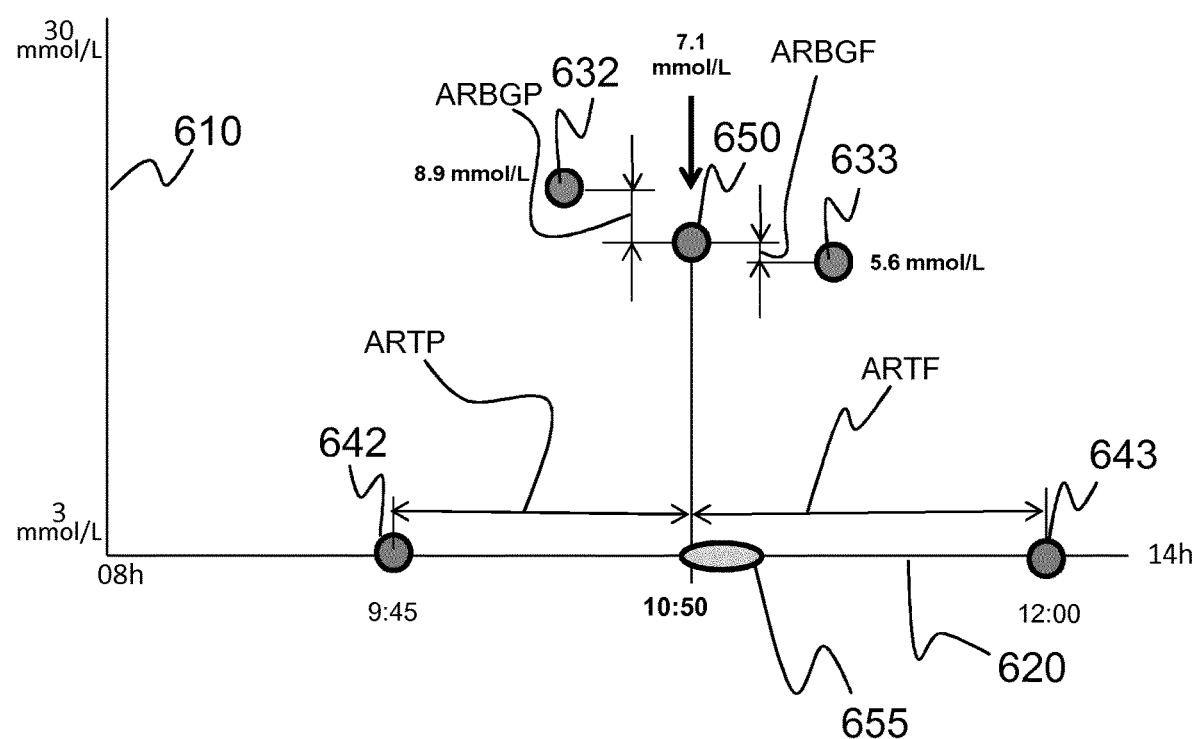

One region of FIG. 7 is depicted in FIGS. 8 and 9 in an enlarged form. FIG. 8 shows a first example for a measurement value 650 and FIG. 9 another example.

In step 502 the absolute difference between the absolute time of the time stamp of the new measurement value 650 and the usual post-breakfast time 642 (closest past time point) is calculated. The result is designated in FIGS. 7 to 9 by ARTP. Analogously, the absolute time difference between the absolute time of the time stamp of the new measurement value 650 and the usual pre-lunch time 643 (closest future time point) is calculated and designated in FIGS. 7 to 9 by ARTF. In the first example depicted in FIG. 8 ARTP=60 min and ARTF=75 min. The second example depicted in FIG. 9 reveals ARTP=65 min and ARTF=70 min.

Further, in step 502 the absolute value of the difference between ARTP and ARTF is calculated D=Abs(ARTP−ARTF). In the first example depicted in FIG. 8 this value is D=15 min and in the second example depicted in FIG. 9 this value is D=5 min.

In step 503 the value D=Abs(ARTP−ARTF) is compared with a predetermined percentage rate of the bigger one of ARTP and ARTF. The percentage rate may be for example 5%, 10 or 15%. The predetermined percentage rate is, in some implementations, stored in the data storage 130 and may be changed by the user or the HCP. In the first example depicted in FIG. 8 for the percentage rate of 15% a value of 11.25 min is calculated and in the second example a value of 10.5 min, wherein in each case ARTF is the bigger value of ARTF and ARTP.

If the difference between ARTP and ARTF is small and within the above mentioned predetermined percentage rate of the bigger one of ARTP and ARTF, then the absolute time of the time stamp of the new measurement value 650 is close to a center time between the closest past time point and the closest future time point. In this region, it can be hardly determined whether the new blood glucose value 650 belongs to the earlier or the later time period, in this case if it is a post-breakfast blood glucose value or a pre-lunch blood glucose value. The time range in which the decision cannot be made, which is called the arbitrary area, is defined as a timespan having a width equal to 2 times the predetermined percentage rate of the bigger one of ARTP and ARTF, wherein the arbitrary area is centered around a mean value of the closest past time point (in this case, the usual post-breakfast time 642) and the closest future time point (in this case, the usual pre-lunch time 643). The arbitrary area is depicted in FIGS. 7 to 9 with the reference number 655.

If the time stamp of the new measurement value 650 is within the arbitrary area 655, another criteria for determining the corresponding tag of an event has to be considered as described below.

If the time stamp of the new measurement value 650 is outside the arbitrary area 655, then the procedure continues with step 509 and choses the closest one of the future or past time point of the usual time points 641, 642, 643, 644, 645, 646, 647 and the corresponding tag is automatically assigned to the new measurement value 650 and provided for confirmation by the user and displayed with a respective sign 168 at the display 162 analogous to the step 140 as explained above for the first tagging calculation rule. This means if ARTP<ARTF the tag of the closest past time point is chosen and if ARTF<ARTP the tag of the closest future time point is assigned. Also analogously the tag sign 168 of the assigned tag is displayed on display 162 and is blinking/flashing and the user may confirm this tag by pressing the confirmation key 152.

With regard to the first example depicted in FIG. 8, D=15 min is compared with 11.25 min (15% of ARTF). As 15 min>11.25 min, the time stamp of the new measurement value 650 is outside the arbitrary area 655 and the event of closest one of the usual time points is chosen and the corresponding tag automatically assigned to the new measurement value 650. Therefore, regarding FIG. 8, the post-breakfast tag 642 is automatically chosen and displayed as explained above.

Alternatively, the user may change the tag using the up and down keys 153, 154 into another tag, if necessary. If the correct tag is chosen, the user confirms the tag by pressing the confirmation key 152. Then, flashing of the displayed tag sign is stopped and the tag sign is displayed continuously without flashing. After confirmation, the processor 140 initiates storage of the associated, confirmed tag with regard to the new measurement value 650 in the data storage 130 via receiving unit 120.

If the value D is within the arbitrary area 655 the procedure continues with step 504.

This is the case for the second example depicted in FIG. 9. Therein, D=5 min and 15% of ARTF=10.5 min which is bigger. The value D lies within the arbitrary area 655.

In the step 504, the values ARBGP and ARBGF are determined. ARBGP is the absolute difference between the median measurement value referring to the event of the closest past time point and the new measurement value, in the present embodiment the absolute difference between the median measurement value referring to the post-breakfast event 632 and the new measurement blood glucose value 650. In FIGS. 7 to 9 the ARBGP is depicted. Accordingly, the value ARBGF is the absolute difference between the new measurement value and the median blood glucose value referring to the event of the closest future time point, in the present case the absolute blood glucose value difference between the new measurement value 650 and the median blood glucose value 633 referring to the pre-lunch event. The value ARBGF is depicted in FIGS. 7 to 9. Therein, the lines ARBGP and ARBGF run parallel to the y-axis 610.

In the second example of FIG. 9 the median measurement value 632 for the post-breakfast tag is 8.9 mmol/L. The median measurement value 633 for the pre-lunch tag is 5.6 mmol/L. The new blood glucose measurement value 650 is 7.1 mmol/L. Accordingly, ARBGP is calculated to 1.8 mmol/L and ARBGF to 1.5 mmol/L.

In the next step 505 the values ARBGP and ARBGF are compared. If ARBGP>ARBGF, then the tag of the closest future time point of the usual time points 641, 642, 643, 644, 645, 646, 647 is chosen in step 506. This means, that the measurement value is closer to the median measurement value of the future time point. This is the case in the second embodiment as shown in FIG. 9 so that in this case the pre-lunch tag is assigned to the new measurement value 650 and shown at the display 162.

Accordingly, if ARBGP<ARBGF the tag of the closest past usual time point is assigned to the new measurement value 650 and displayed at the display 162 in step 507.

If ARBGP=ARBGF, the method proceeds with step 508 and the tag is chosen by comparison of ARTP and ARTF as it is explained for the step 509 above.

As explained above the assigned tag is first shown in a blinking/flashing mode for user confirmation or change. The user may confirm the assigned or chosen tag by the confirmation key 152.

After that, step 510 is reached as depicted in FIG. 6 and the second tagging calculation rule is finished and the methods proceeds with step 390 and 400 as explained below with regard to FIG. 5.

Further, in the "Logbook" mode the user is allowed to change the tag in the above explained manner but only within a predefined time range from the associated time stamp of the blood glucose measurement value, for example within 2 days. In case of the fasting tag, the user may be allowed to change the tag into the fasting tag only within the predefined fasting window around the predefined usual fasting time at the same day.

If the time stamp of the recent measurement value falls within the fasting window around the usual fasting time and there is already a measurement value of that day marked as fasting, the user may be asked which measurement value shall be associated to the fasting tag. After selection of one of the measurement values as the fasting value the selection is confirmed by the user.

Further, if, for example the fasting window around the usual fasting time overlaps with, for example the time range for (pre-meal) breakfast, the fasting tag may have priority over the (pre-meal) breakfast tag in the first tagging calculation rule. Hence, in this case, if no fasting value is recorded for that day, the fasting tag is automatically selected if the time stamp of the present measurement value lies within the fasting window around the usual fasting time and the time range for pre-meal breakfast.

In another embodiment a flashing tag may not only be confirmed by the user by pressing the confirmation key 152 but also by removal of the strip from the port 112 after a blood glucose test, or when the medical device goes into sleep mode.

In the next optional step 390 (see FIG. 5) after finishing the first or the second tagging calculation rule a comment to the present measurement value may be selected by the user using the up and down keys 153, 154. The comment may then be confirmed with the confirmation key 152, wherein the chosen comment is then stored in the data storage 130 associated to the new measurement value as well.

When the medical device 100 is in the "Measure BC" mode, the device may then turn into the sleep state (step 400) automatically after for example 120 seconds without any new action. Once the device has returned a new measurement value, the device turns to the sleep state automatically after for example 60 seconds without any user interaction.

As explained above the medical device 100 provides at least one memory review mode which is called "Logbook" mode. The respective display and calculations are explained in the following.

The "Logbook" mode is entered when the user activates the medical device 100 by pressing e.g. the confirmation button 152. Then a display as depicted in FIG. 3 is shown.

In the "Logbook" the measurement values are, in some implementations, displayed in the order in which the entries are entered into the device or alternatively according to the time and date assigned to the measurement values. In particular the most recent blood glucose measurement value is shown upon entry into the "Logbook" mode. Pressing the up and down keys 153, 154 the user may scroll through the records, for example by pressing the down key 153 the user may scroll backwards in time and by pressing the up key 154 the user scrolls forward in time.

Figure 3:
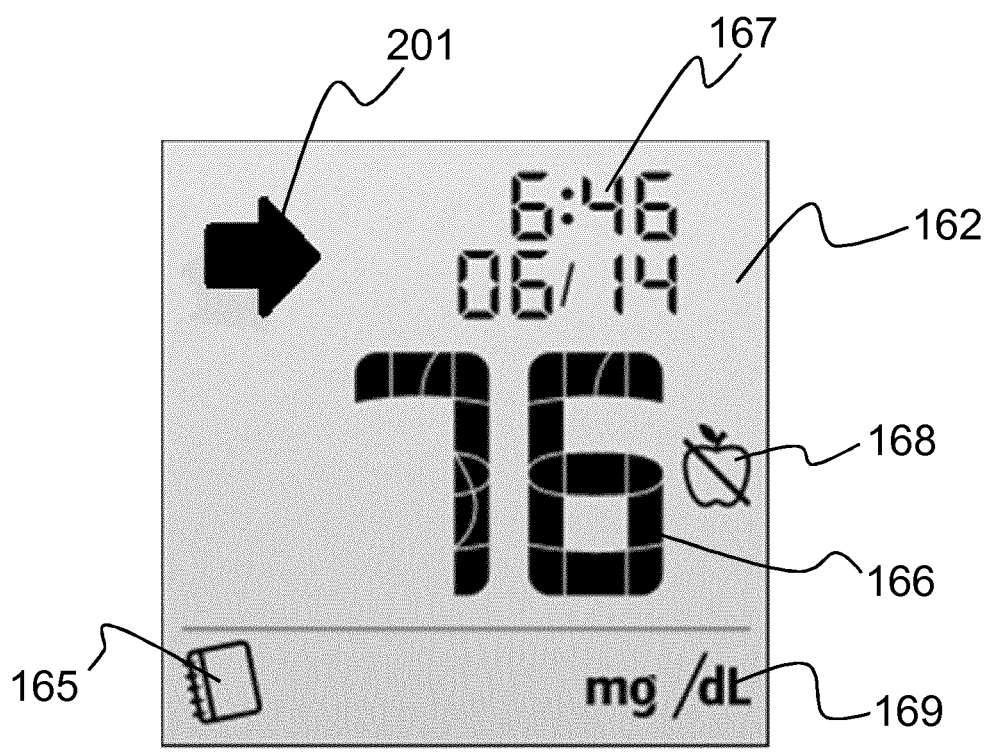
FIG. 3 depicts an example of the display of the medical device as shown in FIG. 1 in a "Logbook" mode.

One Example of a display 162 showing a measurement value is depicted in FIG. 3. The user knows from the "Book" sign 165 in the lower left corner of the display that he/she has entered the "Logbook" mode.

Figure 4:
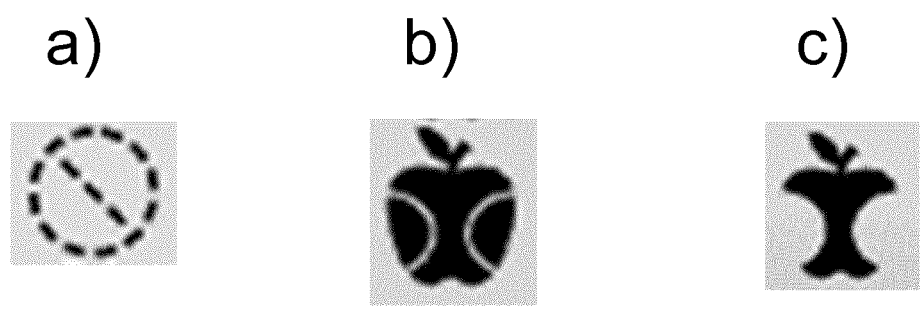
FIG. 4 shows further examples of tag signs as they are displayed on a display of the medical device as shown in FIG. 1.

The display 162 in the "Logbook" mode further shows the blood glucose measurement value 166 as biggest number in the center of the screen. Above the measurement value 166 the associated time stamp 167 including date and time is displayed. On the right side the associated tag as a sign 168 is provided, wherein the sign may show for example an empty, struck out apple as shown at reference number 168 in FIG. 3 in case of an associated fasting tag, a full apple as shown in FIG. 4b) in case of an associated pre-meal tag, a bitten apple as shown in FIG. 4c) in case of an associated post-meal tag or a struck out circle as shown in FIG. 4a) in case of an associated no-tag. Further, the name of the meal (breakfast, lunch, dinner) may be shown above the symbol in the display 162. Additionally, in the lower right corner of the display 162 the unit of measurement 169 for the blood glucose value is provided. A trend information may be provided by an arrow as shown at reference number 201 at the upper left corner of the display 162 in FIG. 3.

As explained above in an example embodiment, device 100 may be realized as a two-part device, wherein the data storage 130, the receiving unit 120, the processor 140, the user input unit 150, the display unit 160 with the display 162, the interface unit 170, and the clock unit 180 form the data management unit and are realized in first part of the device like a smartphone or another computer separate from the measurement unit 110 forming the second part of the device. The method runs as a software program (application or "app") on the hardware of the device. The keys 151, 152, 153 and 154 are realized in this case as button fields on the display of a touchscreen.

LIST OF REFERENCE NUMBERS

100 medical device
110 BG measurement unit
112 slot
120 receiving unit
130 data storage
140 processor
150 user input unit
151, 152, 153, 154 key
160 display unit
162 display
166 blood glucose measurement value
167 time stamp
168 sign of a tag
169 unit of measurement
170 interface
180 clock unit
201 trend information
310, 320, 330, 340, 350, 360 procedure steps
370, 375, 380, 390, 400, 501 procedure steps
502, 503, 504, 505, 506, 507 procedure steps
508, 509, 510 procedure steps
610 y-axis
620 x-axis
631 median measurement value for the fasting tag
632 median measurement value for the post-breakfast tag
633 median measurement value for the pre-lunch tag
634 median measurement value for the post-lunch tag
635 median measurement value for the pre-dinner tag
636 median measurement value for the post-dinner tag
637 median measurement value for the bedtime tag
641 usual fasting time
642 usual post-breakfast time
643 usual pre-lunch time
644 usual post-lunch time 645 usual pre-dinner time
646 usual post-dinner time
647 usual bedtime
650 measurement value
655 arbitrary area
ARTF absolute time difference of the time stamp of the new measurement value from the closest future time point
ARTP absolute time difference of time stamp of the new measurement value from the closest past time point
ARBGP absolute difference between the new measurement value and the median of the previous measurement data referring to the event of the closest past time point
ARBGF absolute difference between the new measurement value and the median of the previous measurement data referring to the event of the closest future time point

The invention claimed is:

1. A medical system comprising:
a blood glucose measurement device arranged to measure blood glucose levels of a patient for generating new measurement values, and
a data management unit for supporting health control of a human body, the data management unit being adapted for automatically monitoring the blood glucose levels of the Patient,
wherein at least one of the blood glucose measurement device or the data management unit comprises a clock, wherein the clock provides date and time information to generate, by the medical system, a corresponding time stamp for each of the new measurement values measured by the blood glucose measurement device,
wherein the data management unit comprises:
a processor,
a receiver communicatively coupled with the processor and adapted to receive, the new measurement values measured by the blood glucose measurement device, wherein the corresponding time stamp of each new measurement value of the new measurement values is at least one of:
if the blood glucose measurement device comprises the clock, received with each new measurement value of the new measurement values, or
if the data management unit comprises the clock, determined by the clock of the data management unit upon receipt by the receiver of each new measurement value of the new measurement values, and
a data storage communicatively coupled with the processor and adapted to store:
instructions for a first tagging calculation rule,
instructions for at least one second tagging calculation rule, and
previously received measurement data indicating previously received measurement values and, for each of the previously received measurement values, a corresponding time stamp, one or more of the previously received measurement values referring to a corresponding tag referring to an event,
wherein, after receipt of a new measurement value of the new measurement values from the receiver, the processor is adapted to process the following steps:
comparing a number of the previously received measurement values stored in the data storage and referring to a corresponding tag to a predetermined minimum value, and
(i) if the number of the previously received measurement values stored in the data storage and referring to a corresponding tag is less than the predetermined minimum value:
automatically assigning a no-tag to the new measurement value, or
automatically assigning the corresponding tag chosen from a group of tags to the new measurement value based on the first tagging calculation rule, wherein the first tagging calculation rule comprises a comparison of the time stamp of the new measurement value with at least a predefined first time range for a first event and at least a predefined second time range for a second event, or
(ii) if the number of the previously received measurement values stored in the data storage and referring to the corresponding tag is equal to or greater than the predetermined minimum value:
automatically assigning the corresponding tag chosen from a group of tags to the new measurement value based on the at least one second tagging calculation rule, comprising:
determining, in accordance with the at least one second tagging calculation rule, an absolute time difference of the time stamp of the new measurement value from the closest past time point of all usual time points (ARTP) and an absolute time difference of the time stamp of the new measurement value from the closest future time point of all usual time points (ARTF),
determining an absolute time difference between the ARTP and the ARTF, and
comparing the absolute time difference between the ARTP and the ARTF with a predetermined percentage rate of the greater of the ARTP and the ARTF, and
(a) if the absolute time difference between the ARTP and the ARTF is larger than the predetermined percentage rate of the greater one of the ARTP and the ARTF, automatically assigning a tag to the new measurement value in accordance with a first criterion in which the tag assigned to the new measurement value in accordance with the first criterion refers to an event for the closer one of the closest future time point and the closest past time point, or
(b) if the absolute time difference between the ARTP and the ARTF is smaller than or equal to the predetermined percentage rate of the greater one of the ARTP and the ARTF, automatically assigning a tag to the new measurement value in accordance with a second criterion distinct from the first criterion.

2. The medical system of claim 1, wherein the receiver comprises the clock.

3. The medical system of claim 1, further comprising a display communicatively coupled with the processor and adapted to at least one of: visibly, audibly, or tangibly display received information,
wherein the display is further adapted to display the automatically assigned tag and requests a user to:
confirm the automatically assigned tag, or
change the automatically assigned tag to another tag and confirm the other tag, and
wherein, after the receiver receives a user confirmation, the processor initiates storing the new measurement value and the corresponding confirmed tag in the data storage.

4. The medical system of claim 1, wherein the at least one second tagging rule comprises adaption of the predefined first time range and the at least one predefined second time range according to the tags and the time stamps of the previously received measurement data.

5. The medical system of claim 1, wherein the at least one second tagging calculation rule considers the previously received measurement data and the new measurement value.

6. The medical system of claim 1, wherein the second criterion considers the new measurement value.

7. The medical system of claim 6, wherein the at least one second tagging calculation rule calculates, in accordance with the second criterion:
   an absolute difference between the new measurement value and the median of the previously received measurement data referring to the event of the closest past time point (ARBGP), and
   an absolute difference between the new measurement value and the median of the previously received measurement data referring to the event of the closest future time point (ARBGF), wherein:
   if the ARBGP is greater than the ARBGF, the processor, in accordance with the second criterion, assigns, to the new measurement value, the tag of the event of the closest future time point,
   if the ARBGP is smaller than the ARBGF, the processor, in accordance with the second criterion, assigns, to the new measurement value, the tag of the event of the closest past time point,
   if the ARBGP is equal to the ARBGF, the processor, in accordance with the second criterion, compares with the ARTP and the ARTF, wherein
      if the ARTP is greater than the ARTF, the processor, in accordance with the second criterion, assigns, to the new measurement value, the tag of the event of the closest future time point,
      if the ARTP is smaller than or equal to the ARTF, the processor, in accordance with the second criterion, assigns, to the new measurement value, the tag of the event of the closest past time point.

8. The medical system of claim 1, wherein the receiver comprises at least one of the following:
   an input port and output ports of a microprocessor, or
   a bus system.

9. The medical system of claim 1, wherein the medical system is provided as a one-part medical device including the blood glucose measurement device, the clock, and the data management unit.

10. A method for operating a medical system, the medical system comprising:
   a blood glucose measurement device arranged to measure blood glucose levels of a patient for generating new measurement values, and
   a data management unit for supporting health control of a human body, the data management unit being adapted for automatically monitoring the blood glucose levels of the patient,
   wherein at least one of the blood glucose measurement device or the data management unit comprises a clock, wherein the clock provides date and time information to generate, by the medical system, a corresponding time stamp for each of the new measurement values measured by the blood glucose measurement device,
   wherein the data management unit comprises:
   a processor,
   a receiver being communicatively coupled with the processor, and
   a data storage communicatively coupled with the processor and adapted to store:
      instructions for a first tagging calculation rule,
      instructions for at least one the second tagging calculation rule, and
   previous received measurement data indicating previously received measurement values and, for each of the previously received measurement values, a corresponding time stamp, one of more of the previously received measurement values further referring to a corresponding tag referring to an event,
   the method comprising:
   receiving a new measurement value of the new measurement values by the receiver,
   at least one of:
   if the blood glucose measurement device comprises the clock, generating the corresponding time stamp for the new measurement value of the new measurement values by the clock and receiving the corresponding time stamp of the new measurement value with the measurement value, or
   if the data management unit comprises the clock, determining the corresponding time stamp by the clock upon receipt by the receiver of the new measurement value of the new measurement values,
   comparing, by the processor, a number of the previously received measurement values stored in the data storage and referring to a corresponding tag to a predetermined minimum value, and
   (i) if the number of the previously received measurement values stored in the data storage and referring to a corresponding tag is less than the predetermined minimum value:
      automatically assigning, by the processor, a no-tag to the new measurement value, or
      automatically assigning, by the processor, a corresponding tag chosen from a group of tags to the new measurement value based on the first tagging calculation rule, wherein the first tagging calculation rule comprises a comparison of the time stamp of the new measurement value with at least a predefined first
   time range for a first event and at least a predefined second time range for a second event, or
   (ii) if the number of the previously received measurement values stored in the data storage and referring to the corresponding tag is equal to or greater than the predetermined minimum value:
      automatically assigning, by the processor, the corresponding tag chosen from the group of tags to the new measurement value based on the at least one second tagging calculation rule, wherein the automatically assigning comprises:
      determining, in accordance with the at least one second tagging calculation rule and by the processor, an absolute time difference of the time stamp of the new measurement value from the closest past time point of all usual time points (ARTP) and an absolute time difference of the time stamp of the new measurement value from the closest future time point of all usual time points (ARTF),
      determining, by the processor, an absolute time difference between the ARTP and the ARTF, and
      comparing, by the processor, the absolute time difference between the ARTP and the ARTF with a predetermined percentage rate of the greater of the ARTP and the ARTF, and
      (a) if the absolute time difference between the ARTP and the ARTF is larger than the predetermined percentage rate of the greater one of the ARTP and the ARTF, automatically assigning a tag, by the processor, to the new measurement value n accordance with a first criterion in which the tag assigned to the new measurement value in accordance with the first criterion refers to an event for the closer one of the closest future time point and the closest past time point, or (b) if the absolute time difference between the ARTP and the ARTF is smaller than or equal to the predetermined percentage rate of the greater one of the ARTP and the ARTF, automatically assigning a tag to the new measurement value, by the processor, in accordance with a second criterion distinct from the first criterion.

11. The method of claim 10, wherein the at least one second tagging calculation rule comprises adaption of the predefined first time range and the at least one predefined second time range according to the tags and the time stamps of the previously received measurement data.

* * * * *

UNITED STATES PATENT AND TRADEMARK OFFICE
CERTIFICATE OF CORRECTION

| | |
|---|---|
| PATENT NO. | : 11,468,042 B2 |
| APPLICATION NO. | : 16/468476 |
| DATED | : October 11, 2022 |
| INVENTOR(S) | : Lars Berger et al. |

It is certified that error appears in the above-identified patent and that said Letters Patent is hereby corrected as shown below:

In the Claims

Column 25, Line 24, Claim 1, delete "Patient," and insert -- patient, --

Column 28, Line 1, Claim 10, delete "one the" and insert -- one --

Column 29, Line 3, Claim 10, delete "n" and insert -- in --

Signed and Sealed this
Thirteenth Day of December, 2022

Katherine Kelly Vidal
*Director of the United States Patent and Trademark Office*